United States Patent [19]

Tsaklakidis et al.

[11] Patent Number: 5,786,371
[45] Date of Patent: Jul. 28, 1998

[54] PYRIDINE AND PYRIDAZINE DERIVATIVES, PROCESSES FOR THE PRODUCTION THEREOF AND PHARMACEUTICAL AGENTS CONTAINING THESE COMPOUNDS

[75] Inventors: Christos Tsaklakidis, Weinheim; Alfred Mertens, Schriesheim; Gerd Zimmermann, Mannheim; Wolfgang Schäfer, Mannheim; Liesel Dörge, Mannheim, all of Germany

[73] Assignee: Boehringer Mannheim GmbH, Mannheim, Germany

[21] Appl. No.: 875,951

[22] PCT Filed: Feb. 8, 1996

[86] PCT No.: PCT/EP96/00523

§ 371 Date: Aug. 11, 1997

§ 102(e) Date: Aug. 11, 1997

[87] PCT Pub. No.: WO96/24586

PCT Pub. Date: Aug. 15, 1996

[30] Foreign Application Priority Data

Feb. 10, 1995 [DE] Germany .................. 195 04 367.7

[51] Int. Cl.$^6$ .................................................. A01N 43/40

[52] U.S. Cl. .................. 514/318; 514/252; 544/238; 544/360; 544/364; 546/187; 546/194

[58] Field of Search .................. 514/318, 252; 544/238, 360, 364; 546/187, 194

[56] References Cited

FOREIGN PATENT DOCUMENTS

WO 94/22835  10/1994  WIPO.

*Primary Examiner*—Alan L. Rotman
*Assistant Examiner*—Garth M. Dahlen
*Attorney, Agent, or Firm*—Nikaido, Marmelstein, Murray & Oram LLP

[57] ABSTRACT

Compounds of Formula I

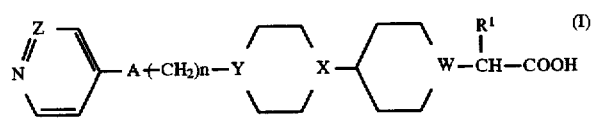

in which the variables are defined herein, processes for the production thereof as well as pharmaceutical agents containing these compounds for the treatment of diseases which are the result of thromboembolytic events.

16 Claims, No Drawings

PYRIDINE AND PYRIDAZINE DERIVATIVES, PROCESSES FOR THE PRODUCTION THEREOF AND PHARMACEUTICAL AGENTS CONTAINING THESE COMPOUNDS

It is known that compounds which carry a basic and an acidic group are capable of inhibiting the aggregation of blood platelets when the basic and the acidic group in the compounds are at a very specific distance from one another (Drugs of the Future 19 (8), 757 (1994). Compounds with an anti-aggregatory action on blood platelets are described in the patent specifications WO 93/14077, EP0537980 A1, EP0542363 A2, WO 94/22834 and WO 94/22835.

The present invention concerns new pyridine and pyridazine derivatives, processes for the production thereof as well as pharmaceutical agents containing these substances.

It was now surprisingly found that pyridine and pyridazine derivatives which additionally carry a carboxylic acid group effectively inhibit the aggregation of blood platelets and can thus be used to treat a wide range of diseases that are due to thromboembolytic events such as stroke, myocardial infarction or arterial occlusive diseases as well as inflammations, osteoporosis or tumour diseases.

The present invention concerns compounds of the general formula I

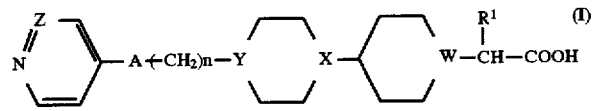

in which $R^1$ denotes hydrogen, lower alkyl, lower alkenyl, cycloalkyl, cycloalkenyl, an optionally substituted monocyclic or bicyclic aryl, an optionally substituted hetaryl, an optionally substituted arylalkyl or one of the groups $-OR^2$, $-NR^3R^4$, W denotes nitrogen or $->CR^5$, X,Y,Z independently of one another denote nitrogen or a group $->CH$ and in the case that W denotes the group $->CR^5$ and X denotes the group $->CH$, Y cannot be the $-CH$ group A denotes oxygen, $>NR^2$ or $>N-P$, n denotes 0-5, p denotes a protecting group for amines such as acetyl, tert.-butyloxycarbonyl or benzyloxycarbonyl, $R^2$ denotes hydrogen, lower alkyl or arylalkyl, $R^3,R^4$ independently of one another denote hydrogen or lower alkyl or together with the nitrogen atom to which they are bound form a five or six-membered heterocyclic ring, $R^5$ denotes hydrogen or a group $-OR^2$, as well as pharmacologically acceptable salts thereof.

In all cases lower alkyl should represent a straight-chained or branched $C_1-C_6$ alkyl group such as e.g. methyl, ethyl, propyl, isopropyl, butyl, isobutyl, pentyl or hexyl in particular methyl, ethyl, propyl, isobutyl and pentyl.

Lower alkenyl denotes unsaturated residues with 3–6 carbon atoms such as allyl, but-2-enyl, hexa-2,4-dienyl but above all allyl.

Cycloalkyl denotes an optionally substituted 3-7-membered ring such as a cyclopropyl, cyclobutyl, cyclopentyl, cyclohexyl or cycloheptyl ring in particular a cyclopropyl, cyclopentyl and cyclohexyl ring. These cycloalkyl residues can be substituted once or twice by a $C_1-C_6$ alkyl group preferably a methyl, ethyl or isopropyl group as well as by hydroxy, methoxy, benzyloxy, amino, methylamino, dimethylamino or benzylamino groups or by chlorine or bromine.

Cycloalkenyl denotes an optionally substituted cyclopentenyl, cyclohexenyl or cycloheptenyl ring. These rings can be substituted once or twice by a $C_1-C_6$ alkyl group preferably a methyl, ethyl or isopropyl group as well as by chlorine, bromine or hydroxy, methoxy, benzyloxy, amino, methylamino, dimethylamino or benzylamino groups.

If the residues $R^3$ and $R^4$ form a heterocyclic ring together with the nitrogen atom to which they are bound then this is a saturated or unsaturated 5–6-membered ring such as a pyrrolidine, piperidine, morpholine or pyrroline ring.

The carbocyclic and heterocyclic rings can be optionally substituted once or twice by $C_1-C_6$ alkyl groups, preferably a methyl, ethyl or isopropyl groups as well as by chlorine, bromine or hydroxy, methoxy, benzyloxy, amino, methylamino, dimethylamino or benzylamino groups.

Aryl usually denotes a phenyl residue which is optionally substituted once or several times.

Hetaryl usually denotes a pyridine, pyridazine, pyrrole, thiophene, furan or imidazole ring which is substituted once or several times.

Bicyclic aryl usually denotes an indane or naphthalene residue which is optionally substituted once or several times, preferably a naphthalene residue.

Aryl, bicyclic aryl and hetaryl residues can be optionally substituted once or several times by $C_1-C_6$ alkyl groups, preferably a methyl, ethyl or isopropyl group as well as by chlorine, bromine, fluorine or hydroxy, alkoxy such as e.g. methoxy, benzyloxy, acetyloxy, carboxy, ethoxycarbonyl, aminocarbonyl, methylaminocarbonyl, dimethylaminocarbonyl, cyano, amino, methylamino, dimethylamino, benzylamino, acetylamino, benzoylamino and amidine groups.

Arylalkyl usually denotes an unsubstituted or once or several-fold substituted benzyl, phenethyl, phenylpropyl, phenylbutyl or phenylpentyl residue, preferably a benzyl, phenethyl or phenylpentyl residue. $C_1-C_6$ alkyl residues, preferably a methyl, ethyl or isopropyl group as well as chlorine, bromine, fluorine or hydroxy, methoxy, benzyloxy, acetyloxy, carboxy, ethoxycarbonyl, aminocarbonyl, methylaminocarbonyl, dimethylaminocarbonyl, cyano, amino, methylamino, dimethylamino, benzylamino, acetylamino, benzoylamino and amidino groups come into consideration as substituents.

n preferably denotes 0, 1 or 2.

Preferred compounds of formula I are compounds in which the ring

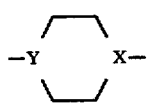

represents a 1,4-piperidinyl or 1,4-piperazenyl ring and the symbols Z, A, W, n and $R^1$ have the stated meaning.

In addition compounds of formula I are preferred in which W represents a >CH or a

residue and the other symbols have the stated meaning.

Compounds of formula I are especially preferred in which A represents the group >NH; n denotes the numbers 0, 1 or 2; the ring

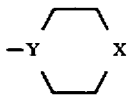

represents a 1,4-piperidinyl or 1,4-piperazinyl ring and W represents a —>CH or —>C—OH residue and Z and $R^1$ have the stated meaning.

Compounds of the general formula I contain at least one asymmetric carbon atom, and therefore optically active compounds of the general formula I are also a subject matter of the present application. Furthermore conformation isomers of compounds of the general formula I which may occur are also a subject matter of the present application.

Compounds of the general formula I are produced according to well-known processes by hydrolyzing an ester of the general formula II

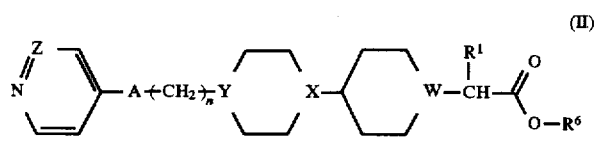

in which $R^1$, A, W, X, Y, Z and n have the meanings stated above and $R^6$ denotes a methyl, ethyl, tert.-butyl or benzyl residue.

Compounds of the general formula II are new and are prepared according to well-known processes and preferably by the following:

a) in the case that W denotes nitrogen, a compound of the general formula III

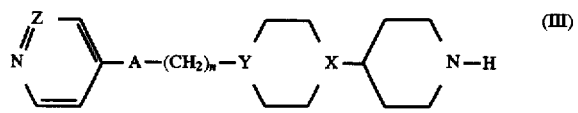

in which A, X, Y, Z and n have the meanings stated above is reacted with a compound of the general formula IV

in which $R^1$ and $R^6$ have the meanings stated above and L denotes a leaving group such as Hal or O—$SO_2$—$R^7$ in which Hal can be chloride, bromide or iodide and $R^7$ can be methyl, phenyl, p-methylphenyl or p-nitrophenyl, b) in the case that W denotes a group $CR^5$ and $R^5$ denotes a group $OR^2$, a ketone of the general formula V

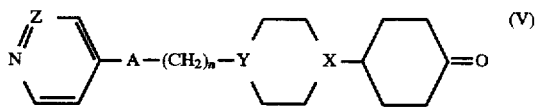

in which A, X, Y, Z and n have the meanings stated above is reacted with a carboxylic acid ester of the general formula VI

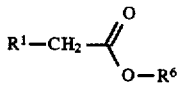

in which $R^1$ and $R^6$ have the meanings stated above and the hydroxyl group of the 2-hydroxy ester which forms in this process of the general formula VII

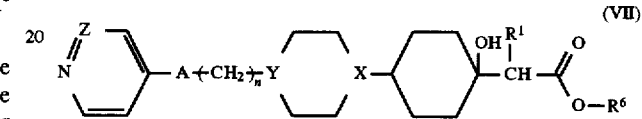

in which $R^1$, $R^6$, X, Y, Z, A and n have the meanings stated above is alkylated if desired with an alkylating agent of the general formula VIII

in which $R^2$ and L have the meanings stated above or c) in the case that W denotes a CH group, a compound of the general formula VI is alkylated with a compound of the general formula IX

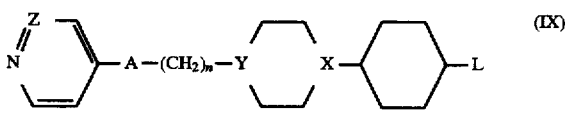

in which A, X, Y, Z, L and n have the meanings stated above or d) the olefinic double bond of a compound of the general formula X

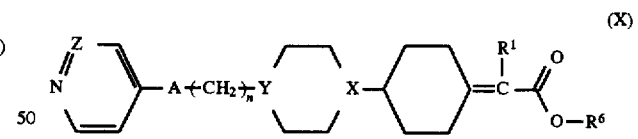

in which A, $R^1$, $R^6$, X, Y, Z and n have the meanings stated above is catalytically hydrogenated.

Compounds of the general formula III are new and are produced according to well-known processes and preferably by the following:

1. in the case that X denotes nitrogen, a compound of the general formula XI

in which P has the meanings stated above is subjected to a reductive amination with an amine of the general formula XII

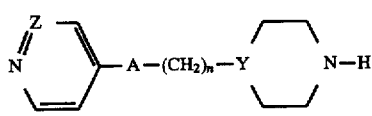

(XII)

in which A, Y, Z and n have the meanings stated above and subsequently the protecting group P is removed from the product that is formed or 2. in the case that X=CH, a compound of the general formula XIII

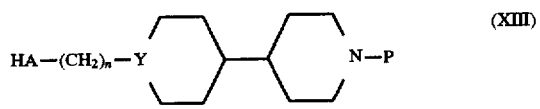

(XIII)

in which A, P, Y and n have the meanings stated above and A cannot be a valency dash if n>0, is reacted with a compound of the general formula XIV

(XIV)

in which Z has the meanings stated above or Z=C—Cl and D has the meaning of L or denotes a nitro group and subsequently the chlorine atoms and the protecting group P is removed from the product.

Compounds of the general formula IV are produced in such a way that in the case that L=Hal, a compound of the general formula VI is halogenated according to processes known in the literature, or in the case that L in formula IV denotes an O—SO$_2$—R$^7$ group, the hydroxyl group of a compound of the general formula XV

(XV)

in which R$^1$ and R$^6$ have the meanings stated above is converted into the corresponding sulfonic acid ester.

Compounds of the general formula V are usually obtained by cleaving the ketal group of a compound of the general formula XVI

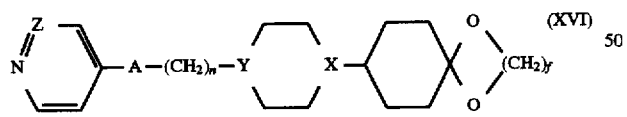

(XVI)

in which A, X, Y, Z and n have the meanings stated above and f=2,3.

Compounds of the general formula VIII can be obtained commercially in the case that L=Hal; in the case that L denotes an O—SO$_2$—R$^7$ group, the hydroxyl group of commercially available alcohols of the general formula XVII

R$^2$—OH (XVII)

in which R$^2$ has the meanings stated above is converted into the corresponding sulfonic acid ester.

If L denotes an O—SO$_2$—R$^7$ group, compounds of the general formula IX are produced by converting the hydroxyl group of a compound of the general formula XVIII,

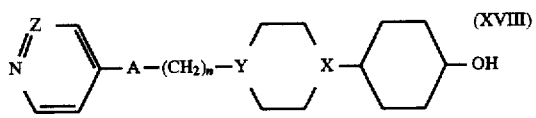

(XVIII)

in which A, X, Y, Z and n have the meanings stated above, into the corresponding sulfonic acid ester; in the case that L=Hal, the hydroxyl group of a compound of the general formula XVIII is nucleophilically substituted by halogen according to processes known from the literature.

Compounds of the general formula X are new and are produced according to a well-known manner by subjecting a ketone of the general formula V to a Wittig reaction with a phosphorane of the general formula XIX.

(XIX)

in which R$^1$ and R$^6$ have the meanings stated above and Ar denotes an aryl within the sense of the definition for aryl given above, or the ketone of formula V is subjected to a Horner-Emmons reaction with a phosphonoacetic acid ester of the general formula XX

(XX)

in which R$^1$ and R6 have the meanings stated above.

Compounds of the general formula XI are prepared in such a way that the commercially available piperidin-4-one is acylated accordingly.

Compounds of the general formula XII are prepared in such a way that a) a compound of the general formula XXI,

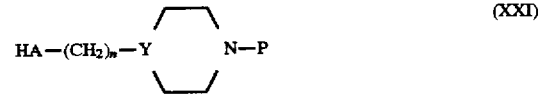

(XXI)

in which A, P, Y and n have the meanings stated above and A cannot be a valency dash if n>0 in the compound XXI, is reacted with a compound of the general formula XIV and the Cl atoms and the protecting group P are removed from the product that is formed or b) a compound of the general formula XXII

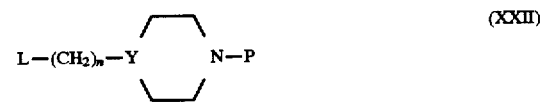

(XXII)

in which P, Y and L have the meanings stated above and n has to be >0 if Y=N is reacted with a compound of the general formula XXIII

(XXIII)

in which A and Z have the meanings stated above except for the valency dash c) in the case that Y=N and n>0 in the compound XII, a piperazine of the general formula XXIV

(XXIV)

in which P has the meanings stated above is reacted with a compound of the general formula XXV

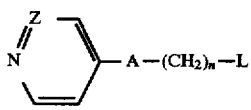
(XXV)

in which A, L, Z and n have the meanings stated above.

Compounds of the general formula XIII are produced in a well-known manner by reductively aminating a ketone of the general formula XI with an amine of the general formula XXVI

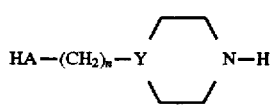
(XXVI)

in which A, Y and n have the meanings stated above.

The production of compounds of the general formula XIV is described in the patent specifications DE 4306506 and DE 4306873.

Compounds of the general formula XV can be obtained by oxidizing the corresponding compounds of the general formula VI according to processes in the literature.

Compounds of the general formula XVI are prepared such that 1. if X=N in formula XVI, a ketone of the general formula XXVII,

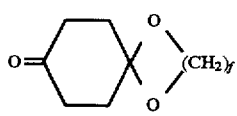
(XXVII)

in which f has the meanings stated above, is hydroaminated with an amine of the general formula XII or 2. if X=CH and Y=N in compounds of formula XVI, an amine of the general formula XXVIII,

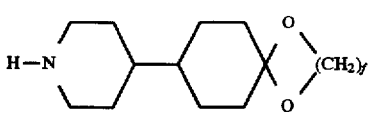
(XXVIII)

in which f has the meanings stated above, is reacted with a compound of the general formula XXV alcohols of the general formula XVII are commercially available.

Compounds of the general formula XVIII are prepared in such a way that 1. if X=N in formula XVIII, a 4-hydroxy-cyclo-hexanone of formula XXIX

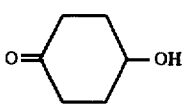
(XXIX)

is reductively aminated with an amine of formula XII or 2. if X=CH and Y=N in compounds of formula XVIII, an amine of formula XXX

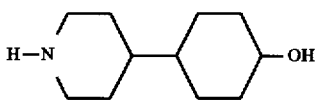
(XXX)

is alkylated with a compound of the general formula XXV.

Some of the compounds of the general formula XIX are commercially available (Aldrich Chemie GmbH and Co. KG) and are obtained in special cases according to known processes by reacting a 2-halogen acid derivative of the general formula IV with a triarylphosphine of the general formula XXXI

AR$_3$P  (XXXI)

in which Ar has the meanings stated above.

Some of the compounds of the general formula XX are commercially available (Aldrich Chemie GmbH and Co. KG) and in special cases are obtained according to known processes by the Arbuzov reaction between a 2-halogencarboxylic acid derivative of formula IV and a trialkylphosphite of the general formula XXXII (OR$^6$)$_3$P  (XXXII)

in which R$^6$ has the meanings stated above.

Compounds of the general formula XXI are prepared in such a way that 1. in the case that Y=N, n>0 and A may not be a valency dash, a compound of the general formula XXXIII, HA—(CH$_2$)n—L  (XXXIII)

in which A, L and n have the meanings stated above, is reacted with a piperazine derivative of formula XXIV or 2. in the case that Y=N and n=0, these are either compounds of the general formula XXIV or a hydrazine of the general formula XXXIV or a hydroxylamine of the general formula XXXV,

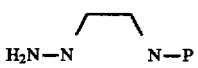
(XXXIV)

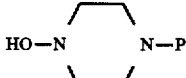
(XXXV)

in which P has the meanings stated above, which are obtainable from compounds of the general formula XXIV.

3) in the case that Y=CH, a carboxylic acid derivative of the general formula XXXVI

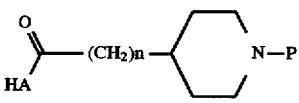
(XXXVI)

in which A, P and n have the meanings stated above is reduced.

Compounds of the general formula XXII are prepared such that 1. in the case that Y=N and n>0, a piperazine of formula XXIV is alkylated with a compound of the general formula XXXVII L—(CH₂)n—L  (XXXVII)

in which L and n have the meanings stated above or 2. in the case that Y=CH, an alcohol of the general formula XXXVIII,

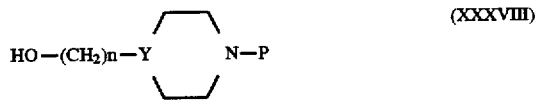
(XXXVIII)

in which P and n have the meanings stated above, is converted into the corresponding sulfonic acid ester or the hydroxyl group is replaced by halogen according to known methods.

Compounds of the general formula XXIII are commercially available.

Compounds of the general formula XXIV are commercially available (Aldrich, GmbH and Co.KG).

Compounds of the general formula XXV are prepared according to known processes in such a way that an alcohol of the general formula XXXIX,

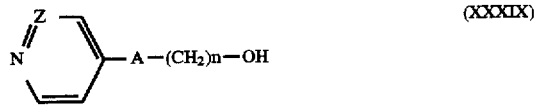
(XXXIX)

in which A, n and Z have the meanings stated above, is converted into the corresponding sulfonic acid ester or the hydroxyl group is replaced by halogen.

Compounds of formula XXVI are prepared by known processes from compounds of formula XXI by hydrolysis of the protecting group P.

Compounds of the general formula XXVII are commercially available (Aldrich-Chemie GmbH and Co.KG).

Compounds of formula XXVIII are obtained according to known processes by ketalizing a ketone of formula XXXX

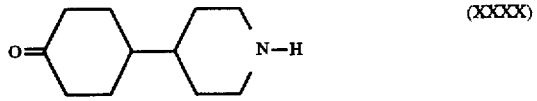
(XXXX)

with a diol of the general formula XXXXI

HO—(CH₂)f—OH  (XXXXI)

in which f has the meanings stated above.

4-Hydroxycyclohexanone of formula XXIX is obtained by appropriately cleaving the ketal group of a compound of the general formula XXXXII

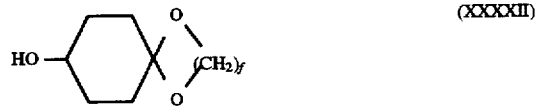
(XXXXII)

in which f has the meanings stated above.

The production of compounds of the general formula XXX is described in the patent specification EP 0537980 A1.

Triarylphosphines of formula XXXI and trialkylphosphites of formula XXXII are commercially available.

In the case that L denotes Hal, compounds of the general formula XXXIII are commercially available and if L denotes a sulfonic acid residue, they are obtained by converting a commercially available alcohol of the general formula XXXXIII HA—(CH₂)n—H  (XXXXIII)

in which A and n have the meanings stated above into a sulfonic acid ester.

Compounds of the general formula XXXIV are prepared by reducing N-nitroso compounds of the general formula XXXXIV

(XXXXIV)

in which P has the meanings stated above.

Compounds of the general formula XXXV are obtained by oxidizing compounds of the general formula XXIV.

Compounds of the general formula XXXVI are produced according to known processes by appropriately acylating a compound of the general formula XXXXV

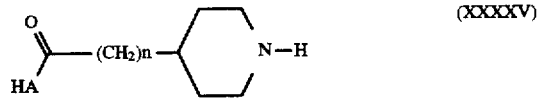
(XXXXV)

in which A and n have the meanings stated above.

In the case that L denotes Hal, compounds of the general formula XXXVII are commercially available and if L denotes a sulfonic acid residue, commercially available 1-omega diols are appropriately sulfonated.

Compounds of the general formula XXXVIII are obtained by reducing compounds of the general formula XXXVI in which A denotes oxygen.

Compounds of the general formula XXXIX are produced by reacting a compound of the general formula XIV with a compound of the general formula XXXXIII and removing the chlorine atoms from the product that is formed.

Compounds of the general formula XXXX are produced by oxidizing an alcohol of formula XXX.

Diols of the general formula XXXXI are commercially available.

Compounds of the general formula XXXXII are obtained by reducing a ketone of the general formula XXVII.

Compounds of the general formula XXXXIV are produced by nitrosating compounds of the general formula XXIV.

Some of the compounds of the general formula XXXXV are commercially available or are described in the literature (Ishihara, Chem. Pharm. Bull. 41, 529 (1993); Merck and Co. EP 478362).

An ester of the general formula II is hydrolyzed to the corresponding carboxylic acid of the general formula I according to the usual methods by treating a carboxylic acid ester of the general formula II in water or in a mixture of water, tetrahydrofuran, dioxane, methanol or ethanol, preferably in a mixture of water/tetrahydrofuran, with a hydroxide such as sodium, potassium or lithium hydroxide, preferably sodium or lithium hydroxide or with an acid such as hydrochloric acid, sulphuric acid or trifluoroacetic acid, preferably trifluoroacetic acid and at temperatures between room temperature and 80° C., preferably at room temperature.

Reaction of a compound of the general formula III with a compound of formula IV or a compound of formula VII with a compound of formula VIII or a compound of formula VI with a compound of formula IX or a compound of formula XXII with a compound of formula XXIII or a compound of formula XXIV with a compound of formula XV or a compound of formula XXVIII with a compound of formula XXV or a compound of formula XXX with a compound of formula XXV or a compound of formula XXIV with a compound of formula XXXIII or a compound of formula XXIV with a compound of formula XXXVII is usually carried out in an aprotic solvent such as toluene, tetrahydrofuran, diethyl ether or dimethyl-formamide, preferably dimethylformamide or tetrahydro-furan using a base such as potassium hydride, sodium hydride, potassium carbonate or sodium bicarbonate, preferably sodium hydride or potassium carbonate and at temperatures between room temperatures and 180° C., preferably at 120° C.

A ketone of the general formula V is reacted with an ester of the general formula VI under the conditions of an aldol reaction in a solvent such as methanol, ethanol, toluene, tetrahydrofuran, diethyl ether or dimethylformamide, preferably tetrahydrofuran or dimethylformamide using a base such as sodium or potassium methylate or sodium or potassium ethylate, sodium hydride, potassium hydride, lithium diisopropylamide, potassium hexamethyl disilazide, preferably sodium hydride or lithium diisopropylamide and at temperatures between −78° C. and 90° C., however, preferably between −78° C. and room temperature.

The catalytic hydrogenation of the olefinic double bond of a compound of the general formula X is carried out analogously to processes known from the literature (A. Nose, Chem. Pharm. Bull. 38, 2097 (1990); Tamura M. Bull. Chem. Soc. Jpn. 53, 561 (1980); Liu H.-J., Synth. Commun. 15, 965 (1985); Chido N., J. Chem. Soc. Chem. Commun. 994 (1990); Büchi G., J. Amer. Chem. Soc. 89, 6745 (1967); Ernst I., Coll. Czech. Chem. Comm. 24, 3341 (1959; Johnson W. S., J. Amer. Chem. Soc. 79, 1995 (1957); Muchowski J. M., Can. J. Chem. 47, 857 (1969)).

The reductive amination of a ketone of formula XI with an amine of formula XII or a ketone of formula XI with an amine of formula XXVI or a ketone of formula XXVII with an amine of formula XII or a ketone of formula XXIX with an amine of formula XII is carried out according to processes known from the literature by reacting the ketone and amine component in a solvent such as methanol or ethanol in the presence of a reducing agent such as sodium cyanoborohydride or sodium acetatoborohydride while adding a Brönsted or Lewis acid such as hydrochloric acid, acetic acid, titanium tetrachloride or titanium tetraisopropylate and at a temperature between 0° C. and 100° C. preferably at room temperature or in the presence of a hydrogenating catalyst such as platinum dioxide and a hydrogen atmosphere (Borch R. F., Org. Synth. Coll. Vol. 6, 499 (1988); Heinzelman R. V. Z. Chem. 8, 270 (1968); Mattson R. J., J. Org. Chem. 55, 2552 (1990); Barney C. L. Tetr. Letters 31, 5547 (1990); Hutchins R. O., J. Org. Chem. 46, 3571 (1981)).

The reaction of a compound of the general formula XIV with a compound of formula XXII or with a compound of formula XXI or with a compound of formula XXXXIII is usually carried out in a solvent such as tetrahydrofuran or 1,4-dioxane, preferably 1,4-dioxane in the presence of a tertiary nitrogen base such as triethylamine or morpholine, preferably triethylamine, and at a temperature between 0° C. and 100° C. preferably, however, at room temperature.

The chlorine atoms of pyridine or pyridazine derivatives containing chlorine can if necessary be removed by catalytic hydrogenation in the presence of a catalyst such as platinum dioxide or palladium on carbon (5–10 percent) in a solvent such as methanol, ethanol or tetrahydrofuran, preferably methanol, and in a hydrogen atmosphere with addition of a base such as sodium methylate, sodium ethylate, potassium carbonate or sodium bicarbonate, preferably potassium carbonate, at a temperature between +10° C. and 80° C. preferably, however, at room temperature and at a reactor pressure between 1 atm and 20 atm, preferably 5 atm.

The protecting group P can if necessary be removed from compounds which carry the protecting group P and which are described in or encompassed by this patent specification by treating a compound carrying the protecting group P with aqueous mineral acids or bases such as hydrochloric acid, sulfuric acid or trifluoroacetic acid or sodium hydroxide solution or potassium hydroxide solution or subjecting it to a catalytic hydrogenation such as e.g. with palladium/carbon/hydrogen.

A compound of the general formula VI or of formula XVIII or of formula XXXVIII or of formula XXXIX is halogenated by reacting it with molecular halogen (chlorine, bromine, iodine), preferably bromine, without a solvent or in an inert solvent such as methylene chloride, chloroform or carbon tetrachloride preferably carbon tetrachloride, and with addition of red phosphorus, phosphorus trichloride or phosphorus tribromide and at a temperature between room temperature and 100° C., preferably at 90° C. (K. Stoh, Chem. Pharm. Bull. 34, 2078 (1986); H. J. Ziegler, Synthesis 1969, 39)). In addition, compounds of the general formula VI can be halogenated by metalation with a lithium amide such as lithium diisopropylamide in an aprotic solvent such as tetrahydrofuran and at a low temperature, preferably at −78° C., and subsequently reacting the compounds of the general formula XVI which are metalized in the α position with bromine, iodine, carbon tetrachloride or carbon tetrabromide (M. Hesse, Helv. Chem. Acta 72, 847 (1989) R. T. Arnold, J. Org. Chem. 43, 3687 (1978)) or with N-chlorosuccinimide or N-bromosuccinimide (W. Oppolzer, Tetrahedron Lett. 26, 5037 (1985).

The hydroxyl group of a compound of the general formula XV, XVII, XVIII, XXXVIII, XXXIX or XXXXIII is converted into a sulfonic acid ester according to the usual methods such as by condensation with a sulfonyl chloride such as methanesulfonyl chloride, benzenesulfonyl chloride, p-toluenesulfonyl chloride or p-nitrobenzene-sulfonyl chloride, preferably methanesulfonyl chloride or p-toluenesulfonyl chloride, in an inert solvent such as methylene chloride, tetrahydrofuran or diethyl ether, preferably methylene chloride, using an auxiliary base such as trimethylamine or triethylamine or pyridine, preferably triethylamine, and at a temperature between 0° C. and room temperature.

Ketal cleavage of a ketal of the general formula XVI or of formula XXXXII or ketalization of a ketone of the general formula XXXX with a diol of formula XXXXI is carried out according to standard procedures in organic chemistry (ORGANIKUM; VEB "Deutscher Verlag der Wissenschaften", Berlin 1977, page 486, 490).

Piperazines of the general formula XXIV are commercially available (Aldrich-Chemie GmbH and Co. KG).

The Wittig reaction between a ketone of the general formula V and a phosphorane of the general formula XIX is carried out according to known methods by reflux heating the reactants in an aprotic solvent such as benzene, toluene or xylol, preferably toluene.

The Horner-Emmons reaction between a ketone of the general formula V and a phosphonoacetic acid ester of the general formula XX is usually carried out in a solvent such as dimethylformamide, tetrahydrofuran, diethyl ether or 1,4-dioxane, preferably dimethylformamide or tetrahydrofuran, using a base such as sodium hydride, butyllithium, lithium diisopropylamide or sodium hexamethyl disilazide, preferably sodium hydride or lithium diisopropylamide, and at a temperature between −78° C. and 100° C. preferably, however, at −78° C. or room temperature.

Oxidation of a compound of the general formula VI to form a compound of the general formula XV is usually carried out in a solvent such as tetrahydrofuran by addition of a base such as lithium diisopropylamide or lithium-N-isopropyl-N-cyclohexylamide using an oxidizing agent such as an oxaziridine derivative, molybdenum peroxide or atmospheric oxygen and at temperatures between −78° C. and room temperature, preferably at 50° C. (C. Tamm, Tetrahedron Lett. 26, 203 (1985); F. A. Davis J. Org. Chem. 51, 2402 (1986); C. Wintoai Synth. Commun. 18, 2141 (1988)).

A compound of the general formula IV is reacted with a triarylphosphine of the general formula XXXI analogously to methods known from the literature (Buddras J., Angew. Chem. 80, 535 (1968); Bestmann H. J. Angew. Chem. 77, 620, 651 (1965); Wittig G. Ber. Deutsch. Chem. Ges. 88, 1654 (1955)).

A compound of the general formula IV is usually reacted with a compound of the general formula XXXII without a solvent at temperatures between room temperature and 150° C., preferably at 130° C., with a reaction time between 30 min and 30 hours, preferably 18 hours.

A carboxylic acid derivative of the general formula XXXVI is usually reduced in a solvent such as tetrahydrofuran or diethyl ether using a reducing agent such as lithium aluminium hydride and at a reaction temperature between 0° C. and the reflux temperature of the solvent used, preferably at 40° C.

A nitroso compound of the general formula XXXXIV is reduced according to known methods by reacting a compound of formula XXXXIV in a solvent such as water, acetic acid, ethanol, tetrahydrofuran or diethyl ether, preferably acetic acid or tetrahydrofuran, with a reducing agent such as elemental zinc, lithium aluminium hydride or sodium aluminium hydride, preferably elemental zinc or lithium aluminium hydride, and at a temperature between room temperature and 120° C., however, preferably at 70° C. A compound of the general formula XXXXIV can also be converted into a compound of formula XXXIV by means of hydrogenolysis using a catalyst such as palladium/carbon (Hatt. H. H., Org. Synth. Coll. Vol. 2, 211 (1943); Schüler F. W., J. Amer. Chem. Soc. 73, 4996 (1951); Schultz M., J. Prakt. Chem. 316, 347 (1974); Smith G. W., Ind. Eng. Chem. Prod. Res. Dev. 1, 117 (1962)).

A hydroxylamine of the general formula XXXV is produced according to known methods by oxidizing an amine of the general formula XXIV in a solvent such as acetone, methanol, water or methylene chloride, preferably methanol or methylene chloride, using an oxidizing agent such as hydrogen peroxide or meta-chloroperbenzoic acid with addition of a catalyst such as sodium tungstate and at a temperature between 0° C. and 60° C. preferably at room temperature (Gorrod J. W., Arch. Pharm. 319, 261 (1986); Sumitomo Chem. Ind. KK. JP 2212363).

A compound of the general formula XXXXV is usually acylated in a solvent such as methylene chloride, dimethylformamide or pyridine, preferably methylene chloride or pyridine, using an acylating agent such as acetyl chloride, di-tert.-butyldicarbonate or benzyloxycarbonyl chloride with addition of an auxiliary base such as triethylamine or 4-dimethylamino pyridine and at a temperature between −10° C. and 50° C., but preferably at room temperature.

An alcohol of the general formula XXX is oxidized to form a ketone of the general formula XXXX according to known methods such as the Jones oxidation (Jones E. R. H., J. Chem. Soc. 36 (1946)), the Swern oxidation (Swern D., Tetrahedron 34, 1651 (1978), the Dess-Martin oxidation (Dess D. B., Martin J. C., J. Org. Chem. 48, 4155 (1983) or using a bromo-urotropine complex as an oxidizing agent (Yavari I., J. Chem. Res. (S) 274 (1994).

A ketone of the general formula XXVII is usually reduced in a solvent such as methanol, ethanol, tetrahydrofuran or diethyl ether, preferably methanol, using a reducing agent such as sodium borohydride, lithium borohydride or lithium aluminium hydride, preferably sodium borohydride, and at a temperature between −10° C. and +30° C., preferably at room temperature.

A compound of the general formula XXIV is usually nitrosated to form a compound of formula XXXXIV using sodium nitrite or isomethyl nitrite in water or ethanol with addition of an acid such as hydrochloric acid or acetic acid and at a temperature between −20° C. and 80° C., preferably at room temperature.

Alkali salts, ammonium salts, trifluoroacetates or hydrochlorides are used above all as pharmacologically acceptable salts which are usually produced for example by titrating the compounds with inorganic or organic bases or acids such as e.g. sodium or potassium bicarbonate, sodium hydroxide solution, potassium hydroxide solution, aqueous ammonia or amines such as trimethylamine or triethylamine, trifluoroacetic acid or hydrochloric acid. The salts are usually purified by precipitation from water/acetone.

The new substances of formula I and salts thereof according to the invention can be administered enterally or parenterally in a liquid or solid form. In this connection all the usual forms of administration come into consideration such as tablets, capsules, dragées, syrups, solutions, suspensions etc. Water is preferably used as the injection medium which contains the usual additives for injection solutions such as stabilizing agents, solubilizers and buffers.

Such additives are for example tartrate and citrate buffer, ethanol, complexing agents (such as ethylenediaminetetraacetic acid and non-toxic salts thereof), high molecular polymers (such as liquid polyethylene oxide) in order to regulate viscosity. Liquid carriers for injection solutions have to be sterile and are preferably dispensed into ampoules. Solid carriers are e.g. starch, lactose, mannitol, methylcellulose, talcum, highly dispersed silicic acids, higher molecular fatty acids (such as stearic acid), gelatine, agar-agar, calcium phosphate, magnesium stearate, animal and vegetable fats, solid high molecular polymers (such as polyethylene glycols); preparations that are suitable for oral application can optionally contain flavourings and sweeteners.

The dose can depend on various factors such as manner of administration, species, age and/or individual state of health. The doses to be administered daily are about 10–1000 mg/human, preferably 100–500 mg/human and can be taken once or several times.

Within the sense of the present invention the following pyridine and pyridazine derivatives are preferred in addition to the compounds mentioned in the examples and compounds derived by combination of all meanings of substituents mentioned in the claims:

1. [4-(3,4,5,6-Tetrahydro-2H-[1,4']-bipyridinyl-4-yl)-cyclohexyl]-acetic acid
2. {4-[4-(Pyridin-4-ylamino-methyl)-piperidin-1-yl]-cyclohexyl}-acetic acid
3. (4-{4-[2-(Pyridin-4-ylamino)-ethyl]-piperidin-1-yl}-cyclohexyl)-acetic acid
4. (4-{4-[3-Pyridin-4-ylamino)-propyl]-piperidin-1-yl}-cyclohexyl)-acetic acid
5. (4-{4-[4-(Pyridin-4-ylamino)-butyl]-piperidin-1-yl}-cyclohexyl)-acetic acid
6. (4-{4-[4-(Pyridin-4-ylamino)-butyl]-piperazin-1-yl}-cyclohexyl)-acetic acid 7. (4-{1-[2-(Pyridin-4-ylamino)-ethyl]-piperidin-4-yl}-cyclohexyl)-acetic acid
8. (4-{1-[3-(Pyridin-4-ylamino)-propyl]-piperidin-4-yl}-cyclohexyl)-acetic acid
9. (4-{1-[4-(Pyridin-4-ylamino)-butyl]-piperidin-4-yl}-cyclohexyl)-acetic acid
10. {1-Hydroxy-4-[1-(pyridin-4-yloxy)-piperidin-4-yl]-cyclohexyl}-acetic acid
11. (1-Hydroxy-4-{4-[2-(pyridin-4-ylamino)-ethyl]-piperidin-1-yl}-cyclohexyl-acetic acid
12. (1-Hydroxy-4-{4-[3-(pyridin-4-ylamino)-propyl]-piperidin-1-yl}-cyclohexyl)-acetic acid m.p. 121°–123° C.
13. (1-Hydroxy-4-{4-[4-(pyridin-4-ylamino)-butyl]-piperidin)-1-yl}-cyclohexyl)-acetic acid
14. (1-Hydroxy-4-{4-[4-(pyridin-4-ylamino)-butyl]-piperazin)-1-yl}-cyclohexyl)-acetic acid
15. [1-Methoxy-4-(4-pyridin-4-yl-piperazin-1-yl)-cyclohexyl]-acetic acid
16. [1-Benzyloxy-4-(4-pyridin-4-yl-piperazin-1-yl)-cyclohexyl]-acetic acid
17. (1-Methoxy-4-{4-[2-(pyridin-4-ylamino)-ethyl]-piperidin-1-yl}-cyclohexyl)-acetic acid
18. (1-Methoxy-4-{4-[2-(pyridin-4-ylamino)ethyl]-piperazin-1-yl}-cyclohexyl)-acetic acid
19. {4-[4-(Pyridin-4-yloxy)-piperazin-1-yl]-piperidin-1-yl}cyclohexyl)-acetic acid
20. {1'-(Pyridin-4-yloxy)-[4,4']bipiperidinyl-1-yl}-acetic acid
21. {1'-[2-(Pyridin-4-ylamino)-ethyl]-[4,4']bipiperidinyl-1-yl}-acetic acid
22. (4-{4-[2-(Pyridin-4-ylamino)-ethyl]-piperazin-1-yl}-piperidin-1-yl)-acetic acid
23. Amino-[4-(3,4,5,6-tetrahydro-2H-[1,4']bipyridinyl-4-yl)-cyclohexyl]-acetic acid
24. (Butyl-1-sulfonylamino)-[4-(3,4,5,6-tetrahydro-2H-[1,4']bipyridinyl-4-yl)-cyclohexyl)-acetic acid
25. (Butyl-1-sulfonylamino)-[1-hydroxy-4-(3,4,5,6-tetrahydro-2H-[1,4']bipyridinyl-4-yl)-cyclohexyl]-acetic acid
26. (Butyl-1-sulfonylamino)-{4-[4-(pyridin-4-ylamino)-piperidin-1-yl]-cyclohexyl}-acetic acid
27. (Butyl-1-sulfonylamino)-[4-(4-pyridin-4-yl-piperazin-1-yl)-cyclohexyl]-acetic acid
28. (Butyl-1-sulfonylamino)-[1-hydroxy-4-(4-pyridin-4-yl-piperazin-1-yl)-cyclohexyl]-acetic acid
29. (Butyl-1-sulfonylamino)-4-{4-[2-(pyridin-4-ylamino)-ethyl]-piperazin-1-yl}-cyclohexyl)-acetic acid
30. (Butyl-1-sulfonylamino)-4-{4-[3-(pyridin-4-ylamino)-propyl]-piperazin-1-yl}-cyclohexyl)-acetic acid
31. (Butyl-1-sulfonylamino)-[1-hydroxy-4-(4-pyridin-4-yl-piperazin-1-yl)-cyclohexyl]-acetic acid
32. {1-Hydroxy-4-[4-(pyridin-4-ylamino)-piperidin-1-yl]-cyclohexyl}-methanesulfonylamino-acetic acid
33. (Butyl-1-sulfonylamino)-{1-hydroxy-4-[4-(pyridin-4-ylamino-methyl)-piperidin-1-yl]-cyclohexyl}-acetic acid
34. (Butyl-1-sulfonylamino)-(1-hydroxy-4-{4-[3-(pyridin-4-ylamino)-propyl]-piperazin-1-yl}-cyclohexyl)-acetic acid
35. Methoxy-[4-(3,4,5,6-tetrahydro-2H-[1,4']bipyridinyl-4-yl)-cyclohexyl]-acetic acid
36. Phenoxy-[4-(4-pyridin-4-yl-piperazin-1-yl)-cyclohexyl]-acetic acid
37. Methoxy-(4-{4-[2-(pyridin-4-ylamino)-ethyl]-piperazin-1-yl}-cyclohexyl)-acetic acid
38. (1-Hydroxy-4-{4-[2-(pyridin-4-ylamino)ethyl]-piperazin-1-yl}-cyclohexyl)-methoxy-acetic acid
39. Methoxy-(4-{4-[3-(pyridin-4-ylamino)-propyl]-piperazin-1-yl}-cyclohexyl)-acetic acid
40. (±)-(1-Hydroxy-4-{4-[4-(pyridin-4-ylamino)-butyl]-piperidin-1-yl}-cyclohexyl)-methoxy-acetic acid
41. [4-(1-Pyridazin-4-yl-piperidin-1-yl)-cyclohexyl]-acetic acid
42. (4-{4-[2-(Pyridazin-4-ylamino)-ethyl]-piperidin-1-yl}-cyclohexyl)-acetic acid
43. (4-{4-[2-(Pyridazin-4-ylamino)-ethyl]-piperazin-1-yl}-cyclohexyl)-acetic acid
44. (4-{4-[4-(Pyridazin-4-ylamino)-butyl]-piperazin-1-yl}-cyclohexyl)-acetic acid
45. (1-Hydroxy-4-{4-[2-(pyridazin-4-ylamino)-ethyl]-piperidin-1-yl}-cyclohexyl)-acetic acid
46. (Butyl-1-sulfonylamino)-(1-hydroxy-4-{4-[2-pyridazin-4-ylamino)-ethyl]-piperidin-1-yl}-cyclohexyl)-acetic acid
47. Methoxy-(4-{4-[2-(pyridazin-4-ylamino)-ethyl]-piperidin-1-yl}-cyclohexyl)-acetic acid
48. {4-[4-(Pyridin-4-yloxy)-piperidin-1-yl]-cyclohexyl}-acetic acid
49. {1-Hydroxy-4-[4-(pyridin-4-yloxy)-piperidin-1-yl]-cyclohexyl}-methoxy-acetic acid
50. {4-[4-(Pyridin-4-yloxy)-piperazin-1-yl]-cyclohexyl}-acetic acid
51. (Butyl-1-sulfonylamino)-{1-hydroxy-4-[4-(pyridin-4-yloxy)-piperazin-1-yl]-cyclohexyl}-acetic acid
52. {4-[1-(Pyridin-4-ylamino)-piperidin-4-yl]-cyclohexyl}-acetic acid
53. {1-Hydroxy-4-[1-(pyridin-4-ylamino)-piperidin-4-yl]-cyclohexyl}-methoxy-acetic acid
54. {4-[4-(Pyridin-4-ylamino)-piperazin-1-yl]-cyclohexyl}-acetic acid
55. (Butyl-1-sulfonylamino)-{1-hydroxy-4-[4-(pyridin-4-yloxy)-piperazin-1-yl]-cyclohexyl}-acetic acid
56. {4-[4-(Pyridazin-4-yloxy)-piperidin-1-yl]-cyclohexyl}-acetic acid
57. {4-[4-(Pyridazin-4-yloxy)-piperazin-1-yl]-cyclohexyl}-acetic acid
58. {1-Hydroxy-4-[4-(pyridazin-4-yloxy)-piperazin-1-yl]-cyclohexyl}-methoxy-acetic acid
59. {4-[1-(Pyridazin-4-ylamino)-piperidin-4-yl]-cyclohexyl}-acetic acid
60. {4-[4-(Pyridazin-4-ylamino)-piperazin-1-yl]-cyclohexyl}-acetic acid
61. (Butyl-1-sulfonylamino)-{1-hydroxy-4-[4-(pyridazin-4-ylamino)-piperazin-1-yl]-cyclohexyl}-acetic acid
62. (4-{3-[(Pyridin-4-ylamino)-propyl]-piperidin-1-yl}-cyclohexyl)-acetic acid m.p. 79°–81° C.

The following examples show several process variants which can be used to synthesize the compounds according to the invention. However, they should not limit the subject matter of the invention. The structure of compounds was established by $^1$H and optionally by $^{13}$C-NMR spectroscopy as well as by mass spectrometry. The purity of the substances was determined by means of C, H, N, and thin layer chromatography.

EXAMPLE 1

[4-[4-(Pyridin-4-ylamino)-piperidin-1-yl]cyclohexyl]-acetic acid a) 115 g 4-hydroxy-phenylacetic acid ethyl ester is hydrogenated in a mixture of 10 ml one molar sodium ethylate solution and 350 ml ethanol for 72 hours at 160° C. and 200 bar using Raney-Nickel. The preparation is subsequently evaporated and the remaining oil is distilled in a high vacuum. 76.4 g 4-hydroxycyclohexane-acetic acid ethyl ester is obtained with a boiling point of 120°–121° C./2 mm Hg. TLC (mobile solvent: dichloromethane/methanol 9:1). Rf=0.8.

b) 20.6 g of the compound obtained from a) was admixed with 130 ml absolute dichloromethane and subsequently 76 g Dess/Martin oxidizing agent (triacetoxyperiodinane, J. Am. Chem. Soc. 113, 7277, 1991) was added. The preparation was stirred for 48 hours at room temperature while cooling occasionally. Subsequently the organic phase was admixed with a saturated sodium bicarbonate solution and it was stirred for 1 hour while mixing thoroughly. The precipitated residue was suction filtered, the organic phase was separated and shaken with sodium hydrogen sulfite and sodium thiosulfate solution. After drying and evaporating the solvent, 16.5 g 4-oxocyclohexane-acetic acid ethyl ester is obtained as an oil. TLC (mobile solvent: dichloromethane/methanol 9:1). Rf=0.9 c) 8.7 g 1-benzyl-4-aminopiperidine, 4.6 g triethylamine and 10 g 4-nitro-2,3,5,6-tetrachloropyridine was added to 100 ml absolute dioxane and stirred for 5 hours at room temperature. After removing dioxane by distillation, the residue was taken up in methylene chloride, admixed with 2 normal hydrochloric acid and stirred vigorously for 30 min. The precipitated precipitate was separated, taken up in a small amount of water, made alkaline with 2 normal ammonia and the aqueous solution was extracted several times with dichloromethane. 13.9 g N-(1-benzylpiperidin-4-yl)-4-amino-2,3,5,6-tetrachloropyridine is obtained as an oil. TLC (mobile solvent: toluene/dioxane/water 9:4.5:0.5). Rf=0.6.

d) 13.8 g of the compound obtained from c) was hydrogenated for 18 hours at room temperature and 40 mbar with addition of 39 g potassium carbonate in a mixture of 100 ml methanol and 100 ml tetrahydrofuran using 1.5 g palladium on carbon (10%). Subsequently the catalyst was removed from this suspension by suction filtration and the filtrate was evaporated. Subsequently the remaining oil was again hydrogenated for 40 hours at room temperature and 4 bar in a mixture of 11 ml glacial acetic acid, 91 ml methanol and 91 ml tetrahydrofuran using 1.8 g palladium on carbon (10%). After separating the catalyst, the solution was evaporated, the residue was admixed with dilute hydrochloric acid and the acidic solution was extracted with dichloromethane. After separating the organic phase the aqueous solution was made alkaline with ammonia and it was concentrated by evaporation. The residue was boiled out for 2 hours with dichloromethane, the undissolved precipitate was separated and the organic phase was dried and evaporated. After crystallizing from acetone, 4.2 g N-(piperidin-4-yl)-4-aminopyridine is obtained from the residue. TLC (mobile solvent: isopropanol/butyl acetate/water/concentrated ammonia 50:30:15:5), Rf=0.2.

e) 0.8 g of the compound obtained from b), 4-oxocyclohexane-acetic acid ethyl ester and 0.9 g of the compound obtained from d) are stirred for 5 days at room temperature in 25 ml methanol with addition of 1.5 ml one molar ethanolic hydrochloric acid and 0.28 g sodium cyanoborohydride. Subsequently the methanol is concentrated by evaporation, the residue is admixed with ether and the organic phase is washed with sodium bicarbonate and sodium chloride solution. After drying and evaporating the ether solution 1.6 g [4-[4-(pyridin-4-ylamino) piperidin-1-yl]cyclohexyl]acetic acid ethyl ester is obtained as an oil. TLC (mobile solvent: isopropanol/butyl acetate/water/concentrated ammonia 50:30:15:5), Rf=0.8.

f) 1.5 g of the compound obtained from e) was stirred in 30 ml methanol and 10 ml one molar NaOH solution for 30 min at 50° C. Subsequently the methanol was evaporated and the residue was extracted twice with dichloromethane after admixing with water. After separating the organic phase, the aqueous phase was applied to an ion exchanger (Dowex 50, acidic form) and after rinsing with water the desired substance was washed from the resin by eluting with ammonia/water 1:3. After evaporating the desired fractions and homogenising the residue with acetone, it was possible to crystallize the residue obtained with ethyl acetate. 360 mg of the title compound [4-[4-(pyridin-4-ylamino)piperidin-1-yl]cyclohexyl]acetic acid is obtained. TLC (mobile solvent: isopropanol/butyl acetate/water/concentrated ammonia 50:30:15:5), Rf=0.2.

EXAMPLE 2

[4-[4-[2-(Pyridin-4-ylamino)ethyl]piperazin-1-yl] cyclohexyl]acetic acid a) A solution of 35.3 g 4-benzylpiperazine-1-acetonitrile in 300 ml absolute ether was slowly added dropwise to a suspension of 8.6 g lithium aluminium hydride in 200 ml absolute ether and stirred for a further 5 hours at room temperature.

Subsequently excess lithium aluminium hydride is carefully decomposed with 25 ml water while cooling on ice. The precipitate is suction filtered, washed with ether and the ether solution is concentrated by evaporation. The remaining oil is distilled in a high vacuum. 16 g 2-(4-benzylpiperazin-1-yl) ethylamine is obtained as an oil with a boiling point of 118°–121° C./0.01 mm Hg.

b) 3.9 g N-[(4-benzyl-piperazin-1-yl)ethyl]-4-amino-2,3,5,6-tetrachloro-pyridine is obtained analogously to example 1c) as an oil from 2.61 g 4-nitro-2,3,5,6-tetrachloronitropyridine, 20 ml absolute dioxane, 2.6 g of the compound obtained in example 2a) and 1.2 g triethylamine after 3 hours at room temperature. TLC (mobile solvent: toluene/dioxane/water 90:20:0.2), Rf=0.61 c) 5 g of the compound obtained from example 2b) was hydrogenated analogously to example 1d) using palladium on carbon (10%). After separating the catalyst and processing, 3.5 g N-[(piperazin-1-yl)ethyl]-4-aminopyridine is obtained as an oil. TLC (mobile solvent: ethyl acetate/methanol saturated with ammonia 85:15), Rf=0.18.

d) 1.6 g [4-[4-[2-(pyridin-4-ylamino)ethyl]piperazin-1-yl]cyclohexyl]acetic acid ethyl ester is obtained analogously to example 1e) as an oil from 2.1 g of the compound from example 2c), 1.62 g of the compound obtained in example 1b) and 0.56 g sodium cyanoborohydride in 50 ml methanol and 3 ml one molar ethanolic hydrochloric acid after stirring for 3 days at room temperature. TLC (mobile solvent: isopropanol/butyl acetate/water/concentrated ammonia 50:30:15:5), Rf=0.58.

e) 0.75 g of the compound obtained in example 2d) is hydrogenated analogously to example 1f) within 30 min at 50° C. in 15 ml methanol and 5 ml one molar NaOH solution. After purifying over an ion exchanger and evaporating the filtrate, the residue obtained is distilled off several times with toluene. The sticky foam which is then obtained can be homogenized with methanol and crystallized. 350 mg [4-[4-[2-(pyridin-4-ylamino)ethyl]piperazin-1-yl] cyclohexyl]acetic acid with a melting point of 220° C. is obtained.

EXAMPLE 3

[4[4[3-(Pyridin-4-ylamino)propyl]piperazin-1-yl] cyclohexyl]acetic acid a) 44 g benzylpiperazine, 200 ml absolute THF, 39.4 g 1-chloro-3-bromopropane and 76 g triethylamine are heated for 8 hours under reflux. After separating the precipitate the tetrahydrofuran is concentrated by evaporation, the residue is dissolved in 500 ml ether, treated twice with carbon and subsequently the solvent is removed by distillation. After distillation in a high vacuum 1-benzyl-4-(3-chloropropyl) piperazine with a boiling point of 145°–148° C./0.3 mm Hg is obtained. 22.75 g of this distillate was dissolved in 200 ml ethanol and admixed with 15 g potassium phthalimide and it was heated for 56 hours under reflux. Subsequently the solvent was evaporated, the residue was dissolved in 150 ml dichloromethane and the organic phase was washed three times with 50 ml two molar sodium hydroxide solution and three times with 50 ml water. Afterwards the organic phase was dried and evaporated. 30 g 2-[3-(4-benzylpiperazin-1-yl)propyl]isoindol-1,3-dione is obtained as a viscous oil. TLC (mobile solvent: heptane/methyl ethyl ketone/ammonia atmosphere 2:1), Rf=0.32.

b) 29.04 g of the compound obtained from example 3a) was heated for 3 hours under reflux with 4.3 ml 98 percent hydrazine hydrate in 150 ml ethanol. The precipitated precipitate is suction filtered and subsequently stirred for 15 min with 100 ml two molar hydrochloric acid while heating gently. Undissolved components are removed by suction filtration and the hydrochloric acid solution was made alkaline and shaken four times with 40 ml dichloromethane. The ethanolic reaction solution from the preparation is also concentrated and combined with the dichloromethane solution. After drying and evaporating, the residue is distilled in a high vacuum. 15.2 g 3-(4-benzylpiperazin-1-yl) propylamine with a boiling point of 144°–146° C./0.01 mm Hg is obtained.

c) 26.1 g 4-nitro-2,3,5,6-tetrachloropyridine, 28 g of the amine obtained from 3b), 12.14 g triethylamine and 200 ml absolute dioxane was reacted and processed analogously to example 1c). 37.5 g N-[(4-benzylpiperazin-1-yl)propyl]-4-amino-2,3,5,6-tetrachloropyridine is obtained as an oil. TLC (mobile solvent: dichloromethane/methyl ethyl ketone/methanol/glacial acetic acid/water 50:17:24:3:5), Rf=0.85.

d) 36 g of the aforementioned compound (example 2c) was hydrogenated on palladium on carbon (10%) and processed analogously to example 1d). 10.2 g N-[3-(piperazin-1-yl)propyl]-4-aminopyridine is obtained as an oil. TLC (mobile solvent: dichloromethane/methanol saturated with ammonia 80:20), Rf=0.62.

e) 2.2 g of the aforementioned compound (example 2d), 1.62 g of the compound obtained from example 1d), 0.56 g sodium cyanoborohydride, 3 ml one molar ethanolic hydrochloric acid and 50 ml methanol are stirred for 3 days at room temperature and subsequently processed analogously to example 1e). 2.6 g [4-[4-[3-(pyridin-4-ylamino)propyl] piperazin-1-yl]cyclohexyl]acetic acid ethyl ester is obtained as an oil. TLC (mobile solvent: isopropanol/butyl acetate/water/concentrated ammonia 50:30:15:5), Rf =0.45.

f) 1.55 g of the aforementioned compound (example 2e) was saponified with 30 ml methanol and 10 ml one molar sodium hydroxide solution and processed analogously to example 1f). After purifying over an ion exchanger the remaining residue is distilled off several times with toluene, subsequently dissolved in a small amount of water, shaken with ethyl acetate and the aqueous phase was evaporated until dryness. 0.61 g [4-[4-[3-(pyridin-4-ylamino)propyl] piperazin-1-yl]cyclohexyl]acetic acid is obtained as a foam after drying over phosphorus pentoxide. TLC (mobile solvent: isopropanol/butyl acetate/water/concentrated ammonia 50:30:15:5), Rf=0.23.

EXAMPLE 4

[4-(4-Pyridin-4-ylpiperazin-1-yl)cyclohexyl]acetic acid a) 1.66 g 1-(4-pyridyl)piperazine, 1.62 g of the compound obtained in example 1g), 0.56 g sodium cyanoborohydride, 3 ml one molar ethanolic hydrochloric acid and 50 ml methanol were stirred for 5 days at room temperature and subsequently processed analogously to example 1e). After purifying by means of column chromatography on silica gel (mobile solvent: ethyl acetate/methanol saturated with ammonia 85:15), 1.6 g [4-(4-pyridin-4-ylpiperazin-1-yl) cyclohexyl]acetic acid ethyl ester is obtained as an oil after evaporating the desired fractions. TLC (mobile solvent: ethyl acetate/methanol saturated with ammonia 85:15), Rf=0.57.

b) 1.6 g of the aforementioned compound (example 4a) was hydrolyzed with 32 ml methanol and 11 ml two molar sodium hydroxide solution and subsequently processed analogously to example 1f). After purifying over an ion exchanger the remaining residue was distilled off several times with toluene and the crystals obtained were twice recrystallized from ethanol. 0.31 g [4-(4-pyridin-4-ylpiperazin-1-yl)cyclohexyl]acetic acid is obtained with a melting point of 225°–227° C.

EXAMPLE 5

[1-Hydroxy-4-[4-pyridin-4-ylamino)piperidin-1-yl] cyclohexyl]acetic acid a) 1.8 g of the compound obtained in example 1d), 2.0 g 1-hydroxy-4-oxocyclohexane-1-acetic acid tert.-butyl ester (prepared analogously to EP 537980), 0.56 g sodium cyanoborohydride, 3 ml one molar ethanolic hydrochloric acid and 50 ml methanol were stirred for 3 days at room temperature and subsequently processed analogously to example 1e). After purifying by means of column chromatography on silica gel (mobile solvent: ethyl acetate/ methanol saturated with ammonia 85:15), 0.62 g [1-hydroxy-4-[4-(pyridin-4-ylamino)piperidin-1-yl [cyclohexyl]acetic acid tert.-butyl ester is obtained as a white foam after evaporating the desired fractions. TLC (mobile solvent: ethyl acetate/methanol saturated with ammonia 85:15), Rf=0.79.

b) 0.62 g of the previous compound (example 5a) was stirred for 20 min at room temperature together with 1 ml water and 10 ml trifluoroacetic acid. After evaporating the solvent, the residue was dissolved in 30 ml saturated sodium bicarbonate solution and purified analogously to example 1f) by means of an ion exchanger. After evaporating the desired fractions, the light beige foam was crystallized by triturating with diethyl ether. 0.41 g [1-hydroxy-4-[4-(pyridin-4-ylamino)piperidin-1-yl]cyclohexyl]acetic acid with a melting point of 261° C. is obtained.

EXAMPLE 6

[1-Hydroxy-4-[4-[2-(pyridin-4-ylamino)ethyl] piperazin-1-yl]cyclohexyl]acetic acid a) 2.1 g of the compound obtained in example 2c), 2.0 g 1-hydroxy-4-oxocyclohexane-1-acetic acid tert.-butyl ester (prepared analogously to EP 537980), 0.56 g sodium cyanoborohydride, 3 ml one molar ethanolic hydrochloric acid and 50 ml methanol were stirred for 5 days at room temperature and subsequently processed analogously to example 1e). After purifying by means of column chromatography on silica gel (mobile solvent: dichloromethane/ methanol saturated with ammonia 85:15), 1.96 g [1-hydroxy-4-[4-[2-(pyridin-4-ylamino)ethyl]-piperazin-1-yl]cyclohexyl]acetic acid tert.-butyl ester is obtained as a white foam after evaporating the desired fractions. TLC (mobile solvent: dichloromethane/methanol saturated with ammonia 85:15), Rf=0.54.

b) 1.9 g of the previous compound (example 6a) was hydrolyzed with 3 ml water and 30 ml trifluoroacetic acid and processed analogously to example 5b). After purifying on an ion exchanger and evaporating the desired fractions, a beige coloured foam is obtained which can be recrystallized from ethanol. 1.2 g [1-hydroxy-4-[4-[2-(pyridin-4-ylamino)ethyl]piperazin-1-yl)cyclohexyl]acetic acid is obtained as white crystals with a melting point of 238°–240° C.

EXAMPLE 7

[1-Hydroxy-4-[4-[3-(pyridin-4-ylamino)propyl] piperazin-1-yl]cyclohexyl]acetic acid a) A white foam is obtained analogously to example 1e) from 2.2 g of the compound obtained in example 3d), 2.0 g 1-hydroxy-4-oxocyclohexane-1-acetic acid tert.-butyl ester (prepared analogously to EP 537980), 0.56 g sodium cyanoborohydride, 3 ml one molar ethanolic hydrochloric acid and 50 ml methanol after stirring for 5 days at room temperature and subsequent processing. After purifying by means of column chromatography on silica gel (mobile solvent: dichloromethane/methanol saturated with ammonia 85:15) and evaporating the desired fractions, 1.5 g [1-hydroxy-4-[4-[3-(pyridin-4-ylamino)propyl]-piperazin-1-yl]cyclohexyl]acetic acid tert.-butyl ester is obtained as a colourless resin. TLC (mobile solvent: dichloromethane/methanol saturated with ammonia 85:15), Rf=0.6.

b) 1.5 g of the previous compound (example 7a) was hydrolysed with 1.5 ml water and 15 ml trifluoroacetic acid and subsequently processed analogously to example 5b). After purifying on an ion exchanger and evaporating the desired fractions, it was possible to crystallize the residue from ethanol. 750 ml [1-hydroxy-4-[4-[3-(pyridin-4-ylamino)propyl]piperazin-1-yl]cyclohexyl]acetic acid is obtained as white crystals with a melting point of 242° C.

EXAMPLE 8

[4-(Pyridin-4-ylaminomethyl)piperidin-1-yl] cyclohexyl]acetic acid a) 1 g 4-nitro-2,3,5,6-tetrachloropyridine, 0.65 g 4-aminomethylpiperidine and 20 ml absolute dioxane were stirred for 1 hour at room temperature. Subsequently the dioxane was removed by distillation, the residue was admixed with water, separated from undissolved material and the aqueous phase was extracted several times with dichloromethane. After drying and evaporating the solvent, the residue can be crystallized from a small amount of diethyl ether. 0.3 g 4-(2,3,5,6-tetrachloropyridin-4-ylaminomethyl)pyridine is obtained as colourless crystals. TLC (mobile solvent: toluene/dioxane/water 90:20:0.2), Rf=0.8.

b) 47 g of the aforementioned compound (example 9a) was hydrogenated within 18 hours at room temperature and at 40 mbar on 5 g palladium on carbon (10%) in 400 ml methanol and 400 ml tetrahydrofuran after adding 164 g potassium carbonate. After separating the catalyst, the solvent was concentrated by evaporation, the remaining residue was dissolved in 150 ml ethanol and a precipitate was precipitated by addition of ethereal hydrochloric acid. The crystallizate was suction filtered, dissolved in 100 ml water, the solution was made alkaline with concentrated ammonia and subsequently shaken several times with dichloromethane. After drying and evaporating the solvent, 9 g 4-(pyridin-4-ylaminomethyl)piperidine is obtained as an oil. TLC (mobile solvent: dichloromethane/methanol saturated with ammonia 85:15), Rf=0.21.

c) 1.95 g of the compound obtained in example 9b), 1.62 g of the compound obtained in example 1d), 0.56 g sodium cyanoborohydride, 3 ml one molar ethanolic hydrochloric acid and 50 ml methanol were stirred for 5 days at room temperature and subsequently processed analogously to example 1e). After purifying by column chromatography on silica gel (mobile solvent: dichloromethane/methanol saturated with ammonia 85:15), 0.5 g [4-[4-(pyridin-4-ylaminomethyl)piperidin-1-yl)cyclohexyl]acetic acid ethyl ester is obtained as a yellow resin after evaporating the desired fractions. TLC (mobile solvent: dichloromethane/methanol saturated with ammonia 85:15), Rf=0.58.

d) 1 g of the aforementioned compound (example 9c) was hydrolyzed twice with 30 ml methanol and 10 ml two molar sodium hydroxide solution and subsequently processed analogously to example 1f). After purifying on an ion exchanger the remaining residue was distilled off several times with toluene and the residue was crystallized from ethanol. 0.38 g [4-[4-(pyridin-4-ylaminomethyl)piperidin-1-yl]cyclohexyl)acetic acid with a melting point of 260° C. is obtained.

EXAMPLE 9

[1-Hydroxy-4-[4-(pyridin-4-ylaminomethyl) piperidin-1-yl]cyclohexyl]acetic acid a) 1.95 g of the compound obtained in example 9b), 2.0 g 1-hydroxy-4-oxocyclohexane-1-acetic acid tert.-butyl ester (prepared according to EP 537980), 0.56 g sodium cyanoborohydride, 3 ml one molar ethanolic hydrochloric acid and 50 ml methanol were dissolved for 5 days at room temperature and subsequently processed analogously to example 1e). After purifying the crude product by column chromatography on silica gel (mobile solvent: ethyl acetate/methanol saturated with ammonia 85:15) and evaporating the desired fractions, 0.55 g [1-hydroxy-4-[4-(pyridin-4-yl-aminomethyl)piperidin-1-yl]cyclohexyl]acetic acid tert.-butyl ester is obtained as a white foam. TLC (mobile solvent: ethyl acetate/methanol saturated with ammonia 85:15), Rf=0.48.

b) 0.51 g of the aforementioned compound (example 10a) is saponified with 1 ml water and 10 ml trifluoroacetic acid and subsequently processed analogously to example 5b). After purifying on an ion exchanger and evaporating the desired fractions it was possible to crystallize the white foam from ethanol. 0.36 g [1-hydroxy-4-[4-(pyridin-4-yl-aminomethyl)piperidin-1-yl)cyclohexyl]acetic acid is obtained as white crystals with a melting point of 266° C.

Pharmacological test

Assay

Microtitre plates are coated overnight with 2 µg/ml isolated activated GpIIb/IIIa receptor. After removing the unbound receptor by washing several times, the surface of the plates is blocked with 1% casein and washed again. The test substance is added in the required concentrations and the plates are incubated for 10 minutes while shaking. The natural ligand of the gpIIb/IIIa receptor, fibrinogen, is added. After 1 hour of incubation the unbound fibrinogen is removed by washing several times and the bound fibrinogen is determined by a peroxidase-conjugated anti-fibrinogen monoclonal antibody by measuring the optical density at 405 nm in an ELISA instrument. Inhibition of a fibrinogen-GpIIb/IIIa interaction results in a low optical density. An $IC_{50}$ is calculated based on a concentration-effect curve.

Literature

The GpIIb/IIIa-Fibrinogen-Elisa is a modification of assays described in the following literature:

Nachman, R. L. & Leung, L. L. K. (1982): Complex formation of platelet membrane glycoproteins IIb and IIIa with fibrinogen. J. Clin. Invest. 69:263–269. Wright, P. S. et al. (1993): An echistatin C-terminal peptide activated GpIbIIIa binding to fibrinogen, fibronectin, vitronectin and collagen type I and type IV. Biochem. J. 293:263–267.

Pharmacological Data

| Example | IC$_{50}$ (µMol/l) |
| --- | --- |
| 5 | 0.14 |
| 12 (page 35) | 0.20 |
| 62 (page 40) | 0.30 |

Comparative experiments

The compound cis-1-hydroxy-4-[4-(4-pyridyl)-piperazin-1-yl]-acetic acid was prepared as a reference substance which is included in the patent WO 94/22835 as example No. 102. This compound has an IC$_{50}$ value of 2.50 µmol/l in the above assay!

We claim:

1. A compound of formula I

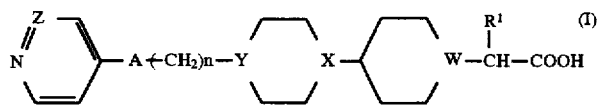

wherein

R$^1$ is a hydrogen atom, C$_1$–C$_6$ alkyl, C$_3$–C$_6$ alkenyl, cycloalkyl, cycloalkenyl, a bicyclic aryl which is either unsubstituted or substituted, a monocyclic aryl which is either unsubstituted or substituted, a hetaryl which is either unsubstituted or substituted, an arylalkyl which is either unsubstituted or substituted, —OR$^2$, or —NR$^3$R$^4$, wherein the bicyclic aryl, monocyclic aryl or hetaryl, when substituted, is substituted by a substituent selected from the group consisting of C$_1$–C$_6$ alkyl, chlorine, bromine, fluorine, hydroxy, and alkoxy, W is a nitrogen atom or —>CR$^5$, X, Y, and Z, each indepdendently are a nitrogen atom or the group —CH, wherein when W is the group —>CR$^5$ and X is the group —>CH, Y is not the group —>CH, A is an oxygen atom, >NR$^2$ or >N—P, n is 0 to 5, P is a protecting group for amines, R$^2$ is a hydrogen atom, C$_1$–C$_6$ alkyl or arylalkyl, wherein the arylalkyl is selected from the group consisting of benzyl, phenethyl, phenylpropyl, phenylbutyl and phenylpentyl residue, and wherein the arylalkyl is either unsubstituted or substituted by a substituent selected from the group consisting of methyl, ethyl, isopropyl, chlorine, bromine, fluorine, hydroxy, methoxy, benzyloxy, acetyloxy, carboxy, ethoxycarbonyl, aminocarbonyl, methylaminocarbonyl, dimethylaminecarbonyl, cyano, amino, methylamino, dimethylamino, benzylamino, acetylamino, benzoylamino and amidino groups, R$^3$ and R$^4$ are each independently a hydrogen atom or C$_1$–C$_6$ alkyl, or R$^3$ and R$^4$, together with the nitrogen atom to which they are both bound, form a five or six-membered heterocyclic ring, R$^5$ is a hydrogen atom or a group —OR$^2$, or an optical isomer or pharmacologically acceptable salt thereof.

2. The compound of claim 1, wherein the ring

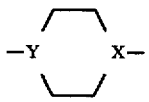

is 1,4-piperidinyl.

3. The compound of claim 1, wherein the ring

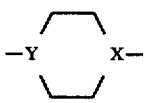

is 1,4-piperazinyl.

4. The compound of claim 1, wherein W is a —>CH or a

residue.

5. The compound of claim 1, wherein A is >NH, n is 0, 1 or 2, the ring

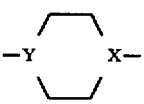

is a 1,4-piperidinyl or 1,4-piperazinyl ring, and W is a —>CH or a —>C—OH residue.

6. The compound of claim 1, wherein the compound is

{4-[4-Pyridin-4-ylamino-methyl)-piperidin-1-yl]-cyclohexyl}-acetic acid;

(4-{4-[2-(Pyridin-4-ylamino)-ethyl]-piperidin-1-yl]-cyclohexyl}-acetic acid;

(4-{4-[3-(Pyridin-4-ylamino)-propyl]-piperidin-1-yl}-cyclohexyl)-acetic acid;

(4-{4-[4-(Pyridin-4-ylamino)-butyl]-piperidin-1-yl}-cyclohexyl)-acetic acid;

(4-{4-[4-(Pyridin-4-ylamino)-butyl]-piperazin-1-yl}-cyclohexyl)-acetic acid;

(4-{1-[2-(Pyridin-4-ylamino)-ethyl]-piperidin-4-yl}-cyclohexyl)-acetic acid;

(4-{1-[3-(Pyridin-4-ylamino)-propyl]-piperidin-4-yl}-cyclohexyl)-acetic acid;

(4-{1-[4-(Pyridin-4-ylamino)-butyl]-piperidin-4-yl}-cyclohexyl)-acetic acid;

{1-Hydroxy-4-[-1-(Pyridin-4-yloxy)-piperidin-4-yl]-cyclohexyl}-acetic acid;

(1-Hydroxy-4-{4-[2-(Pyridin-4-ylamino)-ethyl]-piperidin-1-yl}-cyclohexyl-acetic acid;

(1-Hydroxy-4-{4-[3-(Pyridin-4-ylamino)-propyl]-piperidin-1-yl}-cyclohexyl-acetic acid m. p. 121°–123° C.;

(1-Hydroxy-4-{4-[4-(Pyridin-4-ylamino)-butyl]-piperidin-1-yl}-cyclohexyl)-acetic acid;

(1-Hydroxy-4-{4-[4-(Pyridin-4-ylamino)-butyl]-piperazin-1-yl}-cyclohexyl)-acetic acid;

(1-Methoxy-4-{4-[2-(Pyridin-4-ylamino)-ethyl]-piperidin-1-yl}-cyclohexyl)-acetic acid;

(1-Methoxy-4-{4-[2-(Pyridin-4-ylamino)-ethyl]-piperazin-1-yl}-cyclohexyl)-acetic acid;

{4-[4-(Pyridin-4-yloxy)-piperazin-1-yl]-piperidin-1-yl}cyclohexyl)-acetic acid;
{1'-(Pyridin-4-yloxy)-[4,4']bipiperidinyl-1-yl}-acetic acid;
{1'-[2-(Pyridin-4-ylamino)-ethyl]-[4,4']bipiperidinyl-1-yl}-acetic acid;
(4-{4-[2-(Pyridin-4-ylamino)-ethyl]-piperazin-1-yl}-piperidin-1-yl)-acetic acid;
Methoxy-(4-{4-[2-(Pyridin-4-ylamino)-ethyl]-piperazin-1-yl}-cyclohexyl)-acetic acid;
(1-Hydroxy-4-{4-[2-(Pyridin-4-ylamino)-ethyl]-piperazin-1-yl}-cyclohexyl)-methoxy-acetic acid;
Methoxy-(4-{4-[3-(Pyridin-4-ylamino)-propyl]-piperazin-1-yl}-cyclohexyl)-acetic acid;
(±)-(1-Hydroxy-4-{4-[4-(Pyridin-4-ylamino)-butyl]-piperidin-1-yl}-cyclohexyl)-methoxy-acetic acid;
(4-{4-[2-(Pyridazin-4-ylamino)-ethyl]-piperidin-1-yl}-cyclohexyl)-acetic acid;
(4-{4-[4-(Pyridazin-4-ylamino)-butyl]-piperazin-1-yl}-cyclohexyl)-acetic acid;
(1-Hydroxy-4-{4-[2-(Pyridazin-4-ylamino)-ethyl]-piperidin-1-yl}-cyclohexyl)-acetic acid;
Methoxy-(4-{4-[2-(Pyridazin-4-ylamino)-ethyl]-piperidin-1-yl}-cyclohexyl)-acetic acid;
{4-[4-(Pyridin-4-yloxy)-piperidin-1-yl]-cyclohexyl}-acetic acid;
(1-Hydroxy-4-[4-(Pyridin-4-yloxy)-piperidin-1-yl]-cyclohexyl)-methoxy-acetic acid;
{4-[4-(Pyridin-4-yloxy)-piperazin-1-yl]-cyclohexyl}-acetic acid;
{4-[1-(Pyridin-4-ylamino)-piperidin-4-yl]-cyclohexyl}-acetic acid;
(1-Hydroxy-4-[1-(Pyridin-4-ylamino)-piperidin-4-yl]-cyclohexyl)-methoxy-acetic acid;
{4-[4-(Pyridin-4-ylamino)-piperazin-1-yl]-cyclohexyl}-acetic acid;
{4-[4-(Pyridazin-4-yloxy)-piperidin-1-yl]-cyclohexyl}-acetic acid;
{4-[4-(Pyridazin-4-yloxy)-piperazin-1-yl]-cyclohexyl}-acetic acid;
(1-Hydroxy-4-[4-(Pyridazin-4-yloxy)-piperazin-1-yl]-cyclohexyl}-methoxy-acetic acid;
{4-[1-(Pyridazin-4-ylamino)-piperidin-4-yl]-cyclohexyl}-acetic acid;
{4-[4-(Pyridazin-4-ylamino)-piperazin-1-yl]-cyclohexyl}-acetic acid; or
(4-{3-[(Pyridin-4-ylamino)-propyl]-piperidin-1-yl}-cyclohexyl}-acetic acid m.p. 79°–81° C.

7. The compound of claim 1, wherein the compound is

[4-[4-(Pyridin-4-ylamino)-piperidin-1-yl]-cyclohexyl]-acetic acid;
[4-[4-[2-(Pyridin-4-ylamino)ethyl]piperazin-1-yl]cyclohexyl]-acetic acid;
[4-[4-[3-(Pyridin-4-ylamino)propyl]piperazin-1-yl]cyclohexyl]-acetic acid;
[4-(4-Pyridin-4-ylpiperazin-1-yl)-cyclohexyl]-acetic acid;
[1-Hydroxy-4-[4-Pyridin-4-ylamino)piperidin-1-yl]-cyclohexyl]-acetic acid;
[1-Hydroxy-4-[4-[2-(Pyridin-4-ylamino)ethyl]piperazin-1-yl]-cyclohexyl]-acetic acid;
[1-Hydroxy-4-[4-[3-(Pyridin-4-ylamino)propyl]piperazin-1-yl]-cyclohexyl]-acetic acid;
[4-(Pyridin-4-ylaminomethyl)piperidin-1-yl]-cyclohexyl]-acetic acid; or
[1-Hydroxy-4-[4-(Pyridin-4-ylaminomethyl)piperidin-1-yl]-cyclohexyl]-acetic acid.

8. The compound of claim 1, wherein P is acetyl, tert.-butyloxycarbonyl or benzyloxycarbonyl.

9. A pharmaceutical composition suitable for inhibiting aggregation of blood platelets, comprising at least one compound of formula I

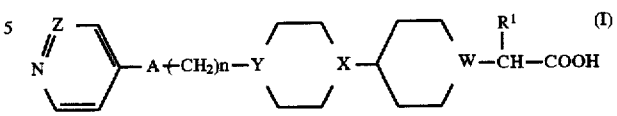

wherein $R^1$ is a hydrogen atom, $C_1-C_6$ alkyl, $C_3-C_6$ alkenyl, cycloalkyl, cycloalkenyl, a bicyclic aryl which is either unsubstituted or substituted, a monocyclic aryl which is either unsubstituted or substituted, a hetaryl which is either unsubstituted or substituted, an arylalkyl which is either unsubstituted or substituted, —$OR^2$, or —$NR^3R^4$, wherein the bicyclic aryl, monocyclic aryl or hetaryl, when substituted, is substituted by a substituent selected from the group consisting of $C_1-C_6$ alkyl, chlorine, bromine, fluorine, hydroxy, and alkoxy, W is a nitrogen atom or —>$CR^5$, X, Y, and Z, each independently are a nitrogen atom or the group —>CH, wherein when W is —>$CR^5$ and X is the group —>CH, Y is not the group —>CH, A is an oxygen atom, >$NR^2$ or >N—P, n is 0 to 5, P is a protecting group for amines, $R^2$ is a hydrogen atom, $C_1-C_6$ alkyl or arylalkyl, wherein the arylalkyl is selected from the group consisting of benzyl, phenethyl, phenylpropyl, phenylbutyl and phenylpentyl residue, and wherein the arylalkyl is either unsubstituted or substituted by a substituent selected from the group consisting of methyl, ethyl, isopropyl, chlorine, bromine, fluorine, hydroxy, methoxy, benzyloxy, acetyloxy, carboxy, ethoxycarbonyl, aminocarbonyl, methylaminocarbonyl, dimethylaminecarbonyl, cyano, amino, methylamino, dimethylamino, benzylamino, acetylamino, benzoylamino and amidino groups, $R^3$ and $R^4$ are each independently a hydrogen atom or $C_1-C_6$ alkyl, or $R^3$ and $R^4$, together with the nitrogen atom to which they are both bound, form a five or six-membered heterocyclic ring, $R^5$ is a hydrogen atom or a group —$OR^2$, or an optical isomer or pharmacologically acceptable salt thereof; and a pharmaceutically acceptable carrier therefor.

10. A method of inhibiting aggregation of blood platelets, comprising the step of administering to a mammal having a disease caused by a thrombo-embolic event an effective amount of a compound of formula I

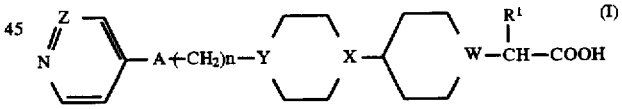

wherein $R^1$ is a hydrogen atom, $C_1-C_6$ alkyl, $C_3-C_6$ alkenyl, cycloalkyl, cycloalkenyl, a bicyclic aryl which is either unsubstituted or substituted, a monocyclic aryl which is either unsubstituted or substituted, a hetaryl which is either unsubstituted or substituted, an arylalkyl which is either unsubstituted or substituted, —$OR^2$, or —$NR^3R^4$, wherein the bicyclic aryl, monocyclic aryl or hetaryl, when substituted, is substituted by a substituent selected from the group consisting of $C_1-C_6$ alkyl, chlorine, bromine, fluorine, hydroxy, and alkoxy, W is a nitrogen atom or —$CR^5$, X, Y, and Z, each indepdendently are a nitrogen atom or the group —CH, wherein when W is —>$CR^5$ and X is the group —>CH, Y is not the group —>CH, A is an oxygen atom, >$NR^2$ or >N—P, n is 0 to 5, P is a protecting group for amines, $R^2$ is a hydrogen atom, $C_1-C_6$ alkyl or arylalkyl, wherein the arylalkyl is selected from the group consisting of benzyl, phenethyl, phenylpropyl, phenylbutyl and phenylpentyl residue, and wherein the arylalkyl is either unsubstituted or substituted by a substituent selected from the group consisting of methyl, ethyl, isopropyl, chlorine, bromine, fluorine, hydroxy, methoxy, benzyloxy, acetyloxy, carboxy, ethoxycarbonyl, aminocarbonyl, methylaminocarbonyl, dimethylaminecarbonyl, cyano, amino, methylamino, dimethylamino, benzylamino, acetylamino, benzoylamino and amidino groups, $R^3$ and $R^4$ are each independently a hydrogen atom or $C_1$–$C_6$ alkyl, or $R^3$ and $R^4$, together with the nitrogen atom to which they are both bound, form a five or six-membered heterocyclic ring, $R^5$ is a hydrogen atom or a group —$OR^2$, or a pharmacologically acceptable salt thereof; conventional carriers; and auxiliary substances.

11. The method of claim 10, wherein the mammal is a human.

12. The method of claim 11, wherein the effective amount is about 10 to 1000 mg/human and the compound is administered at least once each day.

13. The method of claim 10, wherein the compound is administered enterally.

14. The method of claim 10, wherein the compound is administered parenterally.

15. The method of claim 10, wherein the compound is administered in solid form.

16. The method of claim 10, wherein the compound is administered in liquid form.

* * * * *